(12) United States Patent
Liu et al.

(10) Patent No.: US 11,479,616 B2
(45) Date of Patent: Oct. 25, 2022

(54) METHOD FOR PREPARING OKRA POLYGALACTURONIC ACID HAVING URIC ACID-LOWERING EFFECT

(71) Applicant: Institute of Biological and Medical Engineering, Guangdong Academy of Sciences, Guangzhou (CN)

(72) Inventors: Juan Liu, Guangzhou (CN); Junjia Chen, Guangzhou (CN); Chuanli Lu, Guangzhou (CN); Nianfang Ma, Guangzhou (CN); Peizi Kang, Guangzhou (CN)

(73) Assignee: Institute of Biological and Medical Engineering, Guangdong Academy of Sciences, Guangzhou (CN)

( * ) Notice: Subject to any disclaimer, the term of this patent is extended or adjusted under 35 U.S.C. 154(b) by 0 days.

(21) Appl. No.: 17/138,926

(22) Filed: Dec. 31, 2020

(65) Prior Publication Data
US 2022/0025074 A1    Jan. 27, 2022

(30) Foreign Application Priority Data
Jul. 22, 2020   (CN) .......................... 202010709763.9

(51) Int. Cl.
    *C08B 37/00*    (2006.01)
    *A61P 13/12*    (2006.01)
    *A61K 31/715*    (2006.01)

(52) U.S. Cl.
CPC ........ *C08B 37/0048* (2013.01); *A61K 31/715* (2013.01); *A61P 13/12* (2018.01); *A61K 2236/33* (2013.01)

(58) Field of Classification Search
CPC .... C08B 37/0048; A61P 13/12; A61K 31/715

USPC ............................................................ 536/2
See application file for complete search history.

(56) References Cited

PUBLICATIONS

Ren et al. (Food Science, 2010, vol. 31, Issue (13): 110-113).*
Sengkhamparn et al. (Carbohydrate Research 344 (2009) 1824-1832).*
Ozlem Bahadir Acikara (Ion-Exchange Chromatography and Its Applications; Submitted: Jun. 15, 2012, Reviewed: Jan. 8, 2013, Published: Apr. 10, 2013; DOI: 10.5772/55744).*
Ahmed et al. (BM 2013, vol. 4, No. 4, 19-22).*
Qiao et al. (Food and Fermentation Industries 2011, vol. 37, Issue (02): 195-199) (abstract sent).*

* cited by examiner

*Primary Examiner* — Shaojia A Jiang
*Assistant Examiner* — Michael C Henry
(74) *Attorney, Agent, or Firm* — Bayramoglu Law Offices LLC

(57) ABSTRACT

An okra polygalacturonic acid having a uric acid-lowering effect, a method for preparing the same, and use of the same are disclosed. The method includes: smashing an okra, lixiviating the okra in ethanol, and filtering to obtain a filtrate and a residue; removing the filtrate, and lixiviating the residue in heated water to obtain an extraction solution; adding the ethanol into the extraction solution to precipitate okra crude polysaccharides; purifying the okra crude polysaccharides over an anion exchange column by eluting with water or a NaCl solution, a Tris-HCl solution or a NaCl-containing Tris-HCl solution, or a phosphate solution or a NaCl-containing phosphate solution, and collecting a fraction eluted by the NaCl solution, the NaCl-containing Tris-HCl solution, or the NaCl-containing phosphate solution; and concentrating, dialyzing and drying the fraction to obtain the okra polygalacturonic acid.

2 Claims, 2 Drawing Sheets

METHOD FOR PREPARING OKRA POLYGALACTURONIC ACID HAVING URIC ACID-LOWERING EFFECT

CROSS REFERENCE TO THE RELATED APPLICATIONS

This application is based upon and claims priority to Chinese Patent Application No. 202010709763.9, filed on Jul. 22, 2020, the disclosure of which is incorporated herein by reference in its entirety.

TECHNICAL FIELD

The present invention relates to the technical field of agricultural product processing, and particularly relates to an okra polygalacturonic acid having a uric acid-lowering effect, a method for preparing the same, and use of the same.

BACKGROUND

Okra (*Abelmoschus esculentus* (L.) Moench) is an annual herb widely grown in tropical and subtropical regions. Okra is rich in nutrients and bioactive components such as minerals, vitamins, and dietary fiber, and exhibits remarkable benefits such as anti-fatigue effect, reducing blood sugar, relieving constipation, and boosting energy. Okra is also rich in polysaccharides with health functions, the content of which is about 25%; these polysaccharides play a key role in the health effects of okra. Current reports on the uric acid-lowering effect of okra mostly focus on the aqueous extract from okra, but it is not clear whether the uric acid-lowering effect of this aqueous extract is related to polysaccharides. Thus, it is necessary to isolate and purify the active polysaccharides from okra, characterize their structures, and evaluate their uric acid-lowering effects, which are of great significance to clarify the structures and functions of okra polysaccharides.

SUMMARY

A first object of the present invention is to provide an okra polygalacturonic acid having a uric acid-lowering effect.

The inventors have discovered and prepared an okra polygalacturonic acid which is one of the major polysaccharides in okra. The okra polygalacturonic acid has an average molecular weight of 20,459 Da, and consisting of Ara (arabinose) residues, Gal (galactose) residues, and GalA (galacturonic acid) residues at a ratio by weight of 1:2:6.

A second object of the present invention is to provide a method for preparing the okra polygalacturonic acid, which comprises the following steps:

smashing an okra, lixiviating the okra in ethanol, and filtering to give a filtrate and a residue;

removing the filtrate, and lixiviating the residue in heated water to give an extraction solution;

adding ethanol into the extraction solution to precipitate okra crude polysaccharides;

purifying the okra crude polysaccharides over an anion exchange column by eluting with water/NaCl solution, Tris-HCl solution/NaCl-containing Tris-HCl solution, or phosphate solution/NaCl-containing phosphate solution, and collecting a fraction eluted by the NaCl solution, the NaCl-containing Tris-HCl solution, or the NaCl-containing phosphate solution; and concentrating, dialyzing and drying the fraction to give the okra polygalacturonic acid.

Preferably, a NaCl concentration in the NaCl solution, the NaCl-containing Tris-HCl solution, or the NaCl-containing phosphate solution is 1 M.

Preferably, the okra is provided in the form of a fresh okra fruit.

Preferably, the step of lixiviating the residue in heated water is performed by lixiviating the residue in water weighing 1 to 20 times of a weight of the residue for 1-10 hours at a lixiviating temperature of 60° C.-110° C. More preferably, the step of lixiviating the residue in heated water is performed by lixiviating the residue in water weighing 10 to 15 times of the weight of the residue for 2-4 hours at a lixiviating temperature of 105° C.

Preferably, the step of adding ethanol into the extraction solution to precipitate okra crude polysaccharides is performed by adding ethanol to give a final ethanol volume fraction of 10%-90%, and more preferably, by adding ethanol to give a final ethanol volume fraction of 60%.

The uric acid-lowering effect has been evaluated by administrating the okra polygalacturonic acid to mouse models of high uric acid level at a dosage of 200 mg/kg, wherein the blood uric acid level of the mouse models has been significantly reduced after 30 days of administration.

Accordingly, a third object of the present invention is to provide the use of the above-mentioned okra polygalacturonic acid in lowering uric acid, and specifically, a method for lowering uric acid comprising administering to a subject in need thereof the an effective amount of the okra polygalacturonic acid.

A fourth object of the present invention is to provide a composition for lowering uric acid, which comprises the above-mentioned okra polygalacturonic acid or a pharmaceutically acceptable salt thereof as an active ingredient, and a pharmaceutically acceptable carrier.

The inventors have isolated a polygalacturonic acid from okra—the above-mentioned okra polygalacturonic acid—with a yield of 3-6 g/kg and a purity of 85%-95%. The okra polygalacturonic acid exhibits a uric acid-lowering effect, and thus can be used to prepare a uric acid-lowering drug. The present invention provides a new method for preparing an okra polygalacturonic acid, which is of great significance for promoting the value-added processing of okra, improving the technological innovation in agricultural products, and driving industrial transformation and upgrading.

DETAILED DESCRIPTION OF THE EMBODIMENTS

Figure 1:
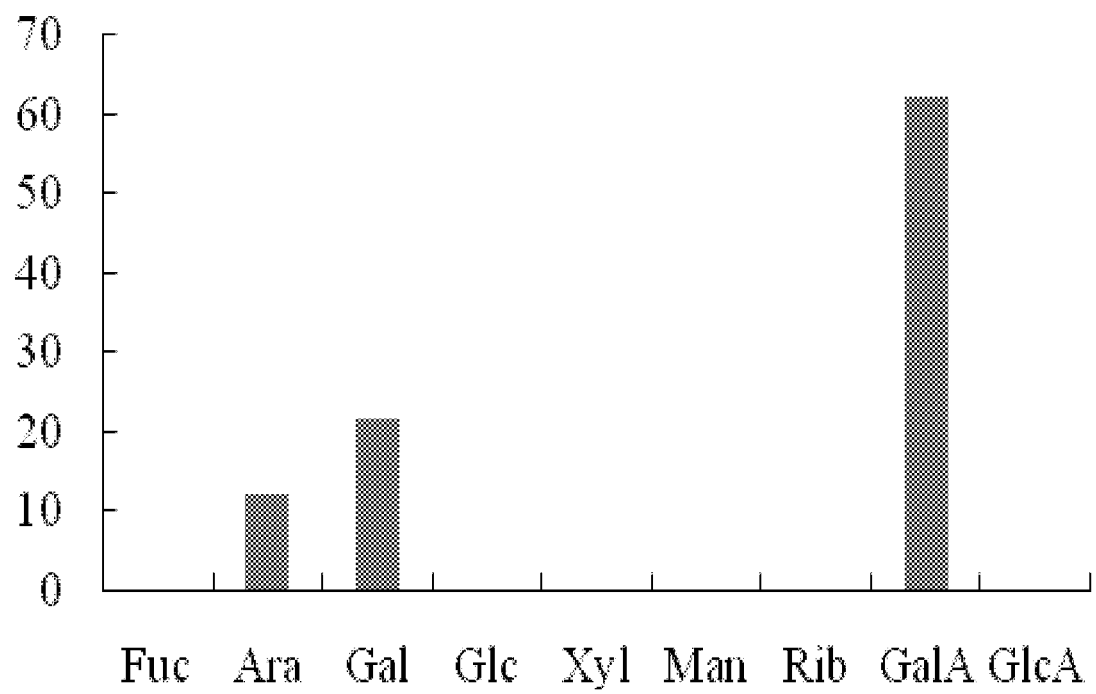
FIG. 1 shows the monosaccharides composing the okra polygalacturonic acid.

The following embodiments are for further illustrating the present invention rather than limiting the invention.

Embodiment 1: Preparation and Isolation, Structural Characterization, and Uric Acid-Lowing Effect Evaluation of the Okra Polygalacturonic Acid 1. Preparation and isolation of the okra polygalacturonic acid
   (1) Fresh okra fruits were washed with distilled water, air dried, and cut into pieces.
   (2) Lixiviation: The okra pieces were lixiviated in ethanol for 7 days at room temperature.
   (3) Extraction of crude polysaccharides: Lixiviation residue was collected, added into deionized water weighing 10 times of a weight of the residue, and lixiviated for 2 hours at 105° C. The resultant mixture was then subjected to filtration using three layers of gauze to remove residues and obtain a filtrate. Ethanol is added to the filtrate to a final ethanol volume fraction of 60%; the resultant mixture was stored at 4° C. for 12 hours, and then centrifuged to collect a precipitate. The precipitate was then subjected to vacuum filtration to remove residual ethanol, and vacuum freeze-dried to give solids which were okra crude polysaccharides.

(4) Purification: The okra crude polysaccharides were purifying over an anion exchange column (DEAE Sepharose Fast Flow) by eluting with water/NaCl solution as the eluting agents. The column was eluted using water first and then a 1 M NaCl solution, respectively with an elution volume of ten times of the column volume. The fraction eluted by the NaCl solution was collected, concentrated, dialyzed using tap water, and vacuum freeze-dried to give the okra polygalacturonic acid.

Through the above method, the yield was 5 g/kg, and the purity of the okra polygalacturonic acid was 95%.

2. Structural characterization of the okra polygalacturonic acid Methods:

(1) Monosaccharide Analysis

An okra polygalacturonic acid sample of 5 mg (±0.05 mg) was precisely weighed out and added into a TFA solution. The resultant mixture was heated at 121° C. for 2 hours and then blow-dried using Nitrogen gas. The residue was washed with methanol and blow dried for 2-3 cycles and then dissolved in sterile water; the resultant solution was transferred to a clean chromatography vial for subsequent test. The test was performed using ion chromatography (ICS 5000, Thermo Fisher Scientific), with an electrochemical detector and a flow rate of 0.5 ml/min. Mobile phase A: ddH$_2$O; mobile phase B: 100 mM NaOH; mobile phase C: 100 mM NaOH/200 mM NaAc. Gradient elution protocol: 0-25 min, phase A maintained at 97.5% and phase B maintained at 2.5%; 25-40 min, phase A changed linearly from 97.5% to 77.5%, phase B maintained at 2.5%, and phase C changed linearly from 0 to 20%; 40-50.1 min, phase A changed linearly from 77.5% to 97.5%, phase B maintained at 2.5%, and phase C changed linearly from 20% to 0; 50.1-60 min, phase A maintained at 97.5% and phase B maintained at 2.5%. The external standard method was used for quantification by making a calibration curve with different concentrations; the content (μg/mg) of each component in the sample was calculated by C*V*F/M, wherein C represents the concentration value obtained from the instrument, V represents the volume (1 mL) of sample solution in one vial, F represents the diluting factor (10), and M represents the total weight of the sample.

(2) Determination of Average Molecular Weight

Determination of average molecular weight of the okra polygalacturonic acid was conducted using high performance gel permeation chromatography (LC-20A, Shimadzu, Kyoto, Japan), with a refractive index detector. Gel columns G6000PWXL, G5000PWXL, and G3000PWXL (Tosoh Bioscience, Stuttgart, Germany) were connected in series. A calibration curve was made using dextran standards with molecular weights of 5.22-150 kDa. The average molecular weight was calculated based on the retention time.

(3) FT-IR Analysis

The spectrum of a dried sample of the okra polygalacturonic acid was obtained using an FT-IR spectrometer (Tensor 27) at the range of 4000-650 cm$^{-1}$.

Results:

As shown in FIG. 1, the okra polygalacturonic acid was soluble in water and consisted of Ara residues, Gal residues, and GalA residues at a ratio by weight of 1:2:6.

Figure 2:
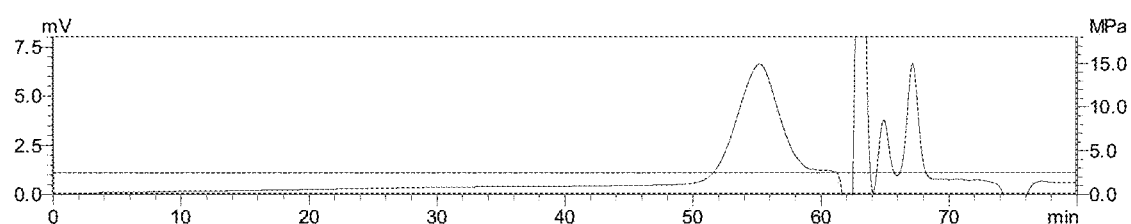
FIG. 2 shows the average molecular weight of the okra polygalacturonic acid.

As shown in FIG. 2, the average molecular weight of the okra polygalacturonic acid is determined to be 20,459 Da by gel chromatography (in FIG. 2, the first peak i.e. the peak at 50-60 min).

Figure 3:
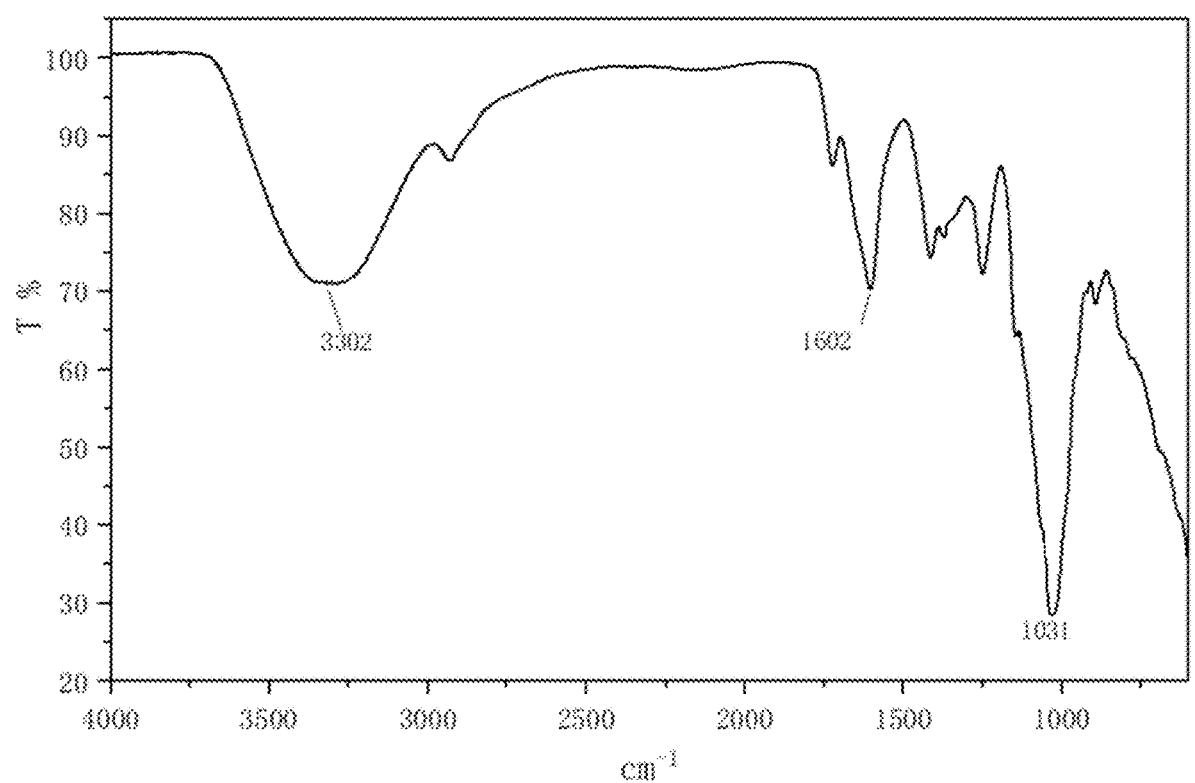
FIG. 3 shows the FT-IR spectrogram of the okra polygalacturonic acid.

As shown in FIG. 3, the FT-IR spectrum of the okra polygalacturonic acid showed a peak at 3302 cm$^{-1}$ representing the stretching vibration of hydroxyl groups, a peak at 1602 cm$^{-1}$ representing the asymmetric stretching vibration, and a strong peak at 1031 cm$^{-1}$ representing the stretching vibration of pendant groups (C—OH) and the vibration of glycosidic bonds (C—O—C), suggesting the presence of one pyranose unit in each polysaccharide molecule.

3. Evaluation of Uric Acid-Lowing Effect of the Okra Polygalacturonic Acid (1) Laboratory Animals C57BL/6 mice (16.7-20.4 g, 6-7 weeks old) were provided by the Guangdong Medical Laboratory Animal Center, and quarantined for 4 days before the trial. During the trial, the mice were kept in a house with stable conditions with a 12 h:12 h light-dark cycle and given ad libitum access to food and water.

(2) Experiment Design

The mice were divided according to their weights into a negative control group (normal mice), a model control group (mice with high uric acid levels), a positive control group (mice with high uric acid levels, administrated with allopurinol tablets), a low-dosage group (mice with high uric acid levels, administrated with 50 mg/kg of the okra polygalacturonic acid), and a high-dosage group (mice with high uric acid levels, administrated with 200 mg/kg of the okra polygalacturonic acid), six mice in each group. The mice of each group were treated with a corresponding solution through intragastric administration with a dosage of 20 mL per kg of body weight, wherein the mice of the positive control group were treated with a 5 mg/mL allopurinol solution, the mice of the negative control group and the model control group were treated with purified water, one administration per day. The mice of the low-dosage and high-dosage groups were respectively treated with a dosage of 50 mg per kg of body weight per day and 200 mg per kg of body weight per day, wherein the samples were dissolved in purified water. The mice were treated for 30 successive days.

The Table 1 below shows how the mice were divided.

TABLE 1

Experiment design for evaluating uric acid-lowing effect of OP1

| Group | n | Dosage mg/kg of body weight | Administration protocol | Volume mL/kg of body weight | Concentration mg/mL |
|---|---|---|---|---|---|
| Negative control | 6 | — | One IA per day for 30 days | 20 | — |

TABLE 1-continued

Experiment design for evaluating uric acid-lowing effect of OP1

| Group | n | Dosage mg/kg of body weight | Administration protocol | Volume mL/kg of body weight | Concentration mg/mL |
|---|---|---|---|---|---|
| Model control | 6 | — | One IA per day for 30 days | 20 | — |
| Positive control | 6 | 100 | One IA per day for 30 days | 20 | 5 |
| OP1 low-dosage | 6 | 50 | One IA per day for 30 days | 20 | 2.5 |
| OP1 high-dosage | 6 | 200 | One IA per day for 30 days | 20 | 10 |

OP1: okra polygalacturonic acid
IA: intragastric administration

Method for preparing OP1 samples: 45 mg of the okra polygalacturonic acid was weighed out and mixed well with a certain volume of purified water. The mixture was further added with purified water to a final volume of 4.5 mL to give a 10 mg/mL high-dosage solution, which shall be shaken well before used. 0.9 mL of the high-dosage solution was added with purified water to a final volume of 3.6 mL and mixed well to give a 2.5 mg/mL low-dosage solution, which shall be shaken well before used.

Method for preparing a 5 mg/mL allopurinol solution: One allopurinol tablet (comprising 0.1 g of the active ingredient per tablet) was ground into powders, then added with a certain volume of 0.5% CMC-Na solution and further ground well. The mixture was then added with 0.5% CMC-Na solution to a final volume of 20 mL and mixed well to give a 5 mg/mL allopurinol solution, which shall be shaken well before used.

(3) Establishment of High Uric Acid Mouse Models

At the day of last administration, the mice of the negative control group were treated with a 0.5% CMC-Na solution with a dosage of 10 mL per kg of body weight by both intraperitoneal and subcutaneous injections, while the mice of the other groups were treated with a 50 mg/mL hypoxanthine solution with a dosage of 10 mL per kg of body weight by intraperitoneal injection (resulting in a dosage of 500 mg per kg of body weight) and a 25 mg/mL potassium oxonate solution with a dosage of 10 mL per kg of body weight by subcutaneous injection (resulting in a dosage of 250 mg per kg of body weight). The last intragastric administration was conducted 30 minutes after establishment of the models.

0.5% CMC-Na solution: 5.0 g of CMC-Na was weighed out precisely and slowly added into a beaker containing about 800 mL of purified water at room temperature under magnetic stirring. The mixture was stirred until CMC-Na was dissolved and then let stand overnight. The next day the solution was transferred to a graduated cylinder to prepare a 1000 mL solution.

50 mg/mL hypoxanthine solution: An appropriate amount of hypoxanthine was weighed out and placed into a mortar followed by the addition of an appropriate volume of 0.5% CMC-Na solution. The mixture was ground well and then added into a 0.5% CMC-Na solution to give a 50 mg/mL solution, which shall be shaken well before used.

25 mg/mL potassium oxonate solution: An appropriate amount of potassium oxonate was weighed out and placed into a mortar followed by the addition of an appropriate volume of 0.5% CMC-Na solution. The mixture was ground well and then added into a 0.5% CMC-Na solution to give a 25 mg/mL solution, which shall be shaken well before used.

(4) Measurement 3 hours after the last administration, the mice were anaesthetized using isoflurane, and blood was collected from each mouse by removing eyeballs. The blood was centrifuged at 3000 rpm for 10 minutes to give serum. Blood uric acid levels, blood creatinine levels, and serum urea nitrogen levels were measured by an automatic biochemical analyzer, and XOD activities were determined using an ELISA kit.

Results were as shown in Table 2. The okra polygalacturonic acid was given to the mice models of the low-dosage group (50 mg/kg) and high-dosage group (200 mg/kg) for 30 days. Compared with the model control group, the high-dosage group exhibited a significantly reduction in uric acid levels of the mice. There was no statistical difference between the high-dosage group and the negative and positive control groups, suggesting that the administration of 200 mg/kg okra polygalacturonic acid (OP1) to mice for 30 days exhibited a uric acid-lowering effect similar to that of the allopurinol tablets and were able to reduce the blood uric acid levels of the high uric acid mice to be similar to those of normal mice.

TABLE 2

Blood uric acid, blood creatinine, serum urea nitrogen, and XOD measurement results
(mean value ± standard deviation; n = 6) after 30-day administration of OP1 to mice

| Group | Dosage mg/kg of body weight | Blood uric acid (μmol/L) | blood creatinine (μmol/L) | serum urea nitrogen (mmol/L) | XOD activity (U/L) |
|---|---|---|---|---|---|
| Negative | — | 133.5 ± 17.5 | 8.8 ± 1.4 | 9.8 ± 0.9 | 32.8 ± 6.9 |
| Model control | — | 186.2 ± 41.9[#] | 35.0 ± 3.1[##] | 19.6 ± 2.6[##] | 30.7 ± 5.0 |
| Positive control | 100 | 134.8 ± 19.9[**] | 30.2 ± 5.7[*] | 23.3 ± 4.1[*] | 19.8 ± 2.2[**] |

TABLE 2-continued

Blood uric acid, blood creatinine, serum urea nitrogen, and XOD measurement results (mean value ± standard deviation; n = 6) after 30-day administration of OP1 to mice

| Group | Dosage mg/kg of body weight | Blood uric acid (μmol/L) | blood creatinine (μmol/L) | serum urea nitrogen (mmol/L) | XOD activity (U/L) |
|---|---|---|---|---|---|
| OP1 low- | 50 | 149.3 ± 18.5* | 41.8 ± 3.3** | 18.8 ± 2.7 | 29.2 ± 2.5 |
| OP1 high- | 200 | 139.0 ± 21.2** | 33.9 ± 2.3 | 17.4 ± 0.9 | 37.1 ± 11.2 |

Note:
1. The t-test was applied to compare the data of the negative control group and the model control group. 2. ANOVA was applied to compare the data of the model control group with the other groups, wherein the serum urea nitrogen data had been log-transformed. 3. When compared with the negative control group: #P < 0.05, ##P < 0.01; when compared with the model control group: *P < 0.05, **P < 0.01.

Embodiment 2

(1) Lixiviation: The okra pieces were lixiviated in ethanol for 7 days at room temperature.
(2) Extraction of crude polysaccharides: Lixiviation residue was collected, added into deionized water weighing 15 times of a weight of the residue, and lixiviated for 4 hours at 105° C. The resultant mixture was then subjected to filtration using three layers of gauze to remove residues and obtain a filtrate. Ethanol is added to the filtrate to a final ethanol volume fraction of 20%; the resultant mixture was stored at 4° C. for 12 hours, and then centrifuged to collect a precipitate. The precipitate was then subjected to vacuum filtration to remove residual ethanol, and vacuum freeze-dried to give solids which were okra crude polysaccharides.
(3) Purification: The okra crude polysaccharides were purifying over an anion exchange column (DEAE Sepharose Fast Flow) by eluting with water/NaCl solution as the eluting agents. The column was eluted using water first and then a 1 M NaCl solution, respectively with an elution volume of ten times of the column volume. The fraction eluted by the NaCl solution was collected, concentrated, dialyzed using tap water, and vacuum freeze-dried to give the okra polygalacturonic acid (identical in structure to the product of embodiment 1).

Through the above method, the yield was 3 g/kg, and the purity of the okra polygalacturonic acid was 90%.

Embodiment 3

(1) Lixiviation: The okra pieces were lixiviated in ethanol for 7 days at room temperature.
(2) Extraction of crude polysaccharides: Lixiviation residue was collected, added into deionized water weighing 10 times of a weight of the residue, and lixiviated for 2 hours at 105° C. The resultant mixture was then subjected to filtration using three layers of gauze to remove residues and obtain a filtrate. Ethanol is added to the filtrate to a final ethanol volume fraction of 60%; the resultant mixture was stored at 4° C. for 12 hours, and then centrifuged to collect a precipitate. The precipitate was then subjected to vacuum filtration to remove residual ethanol, and vacuum freeze-dried to give solids which were okra crude polysaccharides.
(3) Purification: The okra crude polysaccharides were purifying over an anion exchange column (DEAE Sepharose Fast Flow) by eluting with phosphate solution (pH=7.0)/NaCl-containing phosphate solution as the eluting agents. The column was eluted using a phosphate solution (pH=7.0) first and then a phosphate solution (pH=7.0) containing 1 M of NaCl, respectively with an elution volume of ten times of the column volume. The fraction eluted by the NaCl-containing phosphate solution was collected, concentrated, dialyzed using tap water, and vacuum freeze-dried to give the okra polygalacturonic acid (identical in structure to the product of embodiment 1).

Through the above method, the yield was 4 g/kg, and the purity of the okra polygalacturonic acid was 85%.

Embodiment 4

(1) Lixiviation: The okra pieces were lixiviated in ethanol for 7 days at room temperature.
(2) Extraction of crude polysaccharides: Lixiviation residue was collected, added into deionized water weighing 10 times of a weight of the residue, and lixiviated for 2 hours at 105° C. The resultant mixture was then subjected to filtration using three layers of gauze to remove residues and obtain a filtrate. Ethanol is added to the filtrate to a final ethanol volume fraction of 60%; the resultant mixture was stored at 4° C. for 12 hours, and then centrifuged to collect a precipitate. The precipitate was then subjected to vacuum filtration to remove residual ethanol, and vacuum freeze-dried to give solids which were okra crude polysaccharides.
(3) Purification: The okra crude polysaccharides were purifying over an anion exchange column (DEAE Sepharose Fast Flow) by eluting with Tris-HCl solution (pH=8.0)/NaCl-containing Tris-HCl solution as the eluting agents. The column was eluted using a Tris-HCl solution (pH=8.0) first and then a Tris-HCl solution (pH=8.0) containing 1 M of NaCl, respectively with an elution volume of ten times of the column volume. The fraction eluted by the NaCl-containing Tris-HCl solution was collected, concentrated, dialyzed using tap water, and vacuum freeze-dried to give the okra polygalacturonic acid (identical in structure to the product of embodiment 1).

Through the above method, the yield was 4.5 g/kg, and the purity of the okra polygalacturonic acid was 90%.

What is claimed is:

1. A method for preparing an okra polygalacturonic acid, wherein the okra polygalacturonic acid has an average molecular weight of 20,459 Da and consists of arabinose residues, galactose residues, and galacturonic acid residues at a ratio by weight of 1:2:6, and the method comprises the following steps:
    smashing an okra fruit, lixiviating the smashed okra fruit in ethanol, and filtering to obtain a filtrate and a residue;
    removing the filtrate, and lixiviating the residue in water weighing 10 to 15 times of a weight of the residue for 2-4 hours at a lixiviating temperature of 105° C. to obtain an extraction solution;

adding the ethanol into the extraction solution to a final ethanol volume fraction of 60% to precipitate okra crude polysaccharides;

purifying the okra crude polysaccharides over an anion exchange column by eluting with water/NaCl solution, Tris-HCl solution/NaCl-containing Tris-HCl solution, or phosphate solution/NaCl-containing phosphate solution, and collecting a fraction eluted by the NaCl solution, the NaCl-containing Tris-HCl solution, or the NaCl-containing phosphate solution, wherein a NaCl concentration in the NaCl solution, the NaCl-containing Tris-HCl solution, or the NaCl-containing phosphate solution is 1 M; and concentrating, dialyzing and drying the fraction to obtain the okra polygalacturonic acid.

2. The method of claim 1, wherein the okra fruit is provided in a form of a fresh okra fruit.

* * * * *